US012696939B2

(12) United States Patent
Seitz

(10) Patent No.: US 12,696,939 B2
(45) Date of Patent: Aug. 4, 2026

(54) FIT ARRAY FOR DURABLE UNDERWEAR

(71) Applicant: The Procter & Gamble Company,
Cincinnati, OH (US)

(72) Inventor: Bret Darren Seitz, West Chester, OH
(US)

(73) Assignee: **THE PROCTER & GAMBLE
COMPANY**, Cincinnati, OH (US)

( * ) Notice: Subject to any disclaimer, the term of this
patent is extended or adjusted under 35
U.S.C. 154(b) by 702 days.

(21) Appl. No.: 17/990,115

(22) Filed: Nov. 18, 2022

(65) Prior Publication Data

US 2023/0157375 A1     May 25, 2023

Related U.S. Application Data

(60) Provisional application No. 63/281,108, filed on Nov.
19, 2021.

(51) Int. Cl.
| *A61F 13/15* | (2006.01) |
| *A41B 9/00* | (2006.01) |
| *A61F 13/49* | (2006.01) |

(52) U.S. Cl.
CPC ........ *A41B 9/001* (2013.01); *A61F 13/49006*
(2013.01)

(58) Field of Classification Search
CPC ................................ A41B 9/001; A61F 13/49
USPC ........................................................ 604/396
See application file for complete search history.

(56) References Cited

U.S. PATENT DOCUMENTS

| 2,705,957 A | 4/1955 | Virginia |
| 3,909,851 A | 10/1975 | Garrou et al. |

| 4,355,425 A | 10/1982 | Jones et al. |
| 5,085,653 A | 2/1992 | Levy |
| 5,248,309 A | 9/1993 | Serbiak |
| (Continued) | | |

FOREIGN PATENT DOCUMENTS

| CA | 2255465 A1 | 6/2000 |
| CA | 2827795 A1 | 11/2013 |
| (Continued) | | |

OTHER PUBLICATIONS

16165 PCT Search Report and Written Opinion for PCT/US2022/
077840 dated Feb. 3, 2023, 14 pages.

(Continued)

*Primary Examiner* — Jacqueline F Stephens

(74) *Attorney, Agent, or Firm* — Sarah M. DeCristofaro

(57) ABSTRACT

Arrays of durable absorbent underwear pants having common cut style designations are disclosed. Each of the arrays includes pants of a common cut style designation and a plurality of differing size designations. In some examples pants of differing size designations in the arrays are sized such that, with each step up in size designation to an adjacent larger size designation, the associated amount or percentage of increase in actual pant hip and/or waist size is equal to, or decreases, as compared to the increase associated with the preceding step up. In some examples pants of differing size designations are sized such that, with each step up in size designation to an adjacent larger size designation, the difference between actual pant hip size and actual pant waist size decreases. The disclosed sizing practices reflect discoveries of wearers' preferences for differences in fit, with differences in body sizes.

17 Claims, 8 Drawing Sheets

(56) References Cited

U.S. PATENT DOCUMENTS

| | | | |
|---|---|---|---|
| 5,562,648 A | 10/1996 | Peterson | |
| 5,851,204 A | 12/1998 | Mizutani | |
| 6,258,455 B1 | 7/2001 | Clarke | |
| 6,287,286 B1 | 9/2001 | Akin et al. | |
| 6,393,621 B1 | 5/2002 | Redwine et al. | |
| 6,884,494 B1 | 4/2005 | Curro | |
| 7,118,639 B2 | 10/2006 | Delucia et al. | |
| 7,322,966 B1 | 1/2008 | Deerin | |
| 7,458,961 B2 | 12/2008 | Carstens | |
| 7,462,173 B2 | 12/2008 | Carstens | |
| 7,846,145 B2 | 12/2010 | Carstens | |
| 8,099,794 B2 | 1/2012 | Carstens | |
| 8,117,675 B2 | 2/2012 | Strange et al. | |
| 8,262,638 B2 | 9/2012 | Carstens | |
| 8,348,918 B2 | 1/2013 | Carstens | |
| 8,454,570 B2 | 6/2013 | Carstens | |
| 8,679,085 B2 | 3/2014 | Ronstroem | |
| 8,998,870 B2 | 4/2015 | Roe | |
| 9,980,861 B2 | 5/2018 | Deerin | |
| 10,441,480 B2 | 10/2019 | Griffiths | |
| 10,966,873 B2 | 4/2021 | Schneider | |
| 11,154,431 B1 | 10/2021 | Yip et al. | |
| 11,207,225 B2 | 12/2021 | Kajanthan | |
| 11,395,774 B2 | 7/2022 | Skinner | |
| 2002/0004349 A1 | 1/2002 | Tsujiyama et al. | |
| 2002/0016580 A1 | 2/2002 | Wada | |
| 2003/0097109 A1 | 5/2003 | Bruce | |
| 2005/0120466 A1 | 6/2005 | Coenen et al. | |
| 2005/0142331 A1 | 6/2005 | Anderson | |
| 2005/0229293 A1 | 10/2005 | Miller | |
| 2006/0070163 A1 | 4/2006 | Beck | |
| 2006/0264869 A1 | 11/2006 | Carstens | |
| 2006/0264883 A1 | 11/2006 | Carstens | |
| 2006/0264884 A1 | 11/2006 | Carstens | |
| 2007/0012519 A1 | 1/2007 | Angielski | |
| 2007/0106354 A1 | 5/2007 | Carstens | |
| 2007/0245449 A1 | 10/2007 | Ehmsen et al. | |
| 2008/0147031 A1* | 6/2008 | Long | A61F 13/42 604/361 |
| 2010/0249736 A1 | 9/2010 | Png et al. | |
| 2011/0172621 A1 | 7/2011 | Lee | |
| 2013/0226120 A1 | 8/2013 | Van De Maele | |
| 2014/0018763 A1 | 1/2014 | Evenson et al. | |
| 2014/0039432 A1 | 2/2014 | Dunbar et al. | |
| 2014/0257228 A1 | 9/2014 | Wang et al. | |
| 2014/0257229 A1 | 9/2014 | Wang et al. | |
| 2014/0378932 A1* | 12/2014 | Seitz | A61F 13/49011 604/385.3 |
| 2015/0272787 A1* | 10/2015 | Seitz | A61F 13/551 604/385.01 |
| 2015/0320611 A1* | 11/2015 | Seitz | A61F 13/496 604/385.01 |

| | | | |
|---|---|---|---|
| 2016/0089276 A1 | 3/2016 | Griffiths | |
| 2016/0100997 A1 | 4/2016 | Seitz | |
| 2016/0166447 A1 | 6/2016 | Toro | |
| 2016/0184146 A1 | 6/2016 | Tulk | |
| 2020/0000155 A1 | 1/2020 | Etienne | |
| 2021/0030605 A1 | 2/2021 | Kajanthan et al. | |
| 2021/0100698 A1 | 4/2021 | Langdon et al. | |
| 2021/0290447 A1 | 9/2021 | Sepello et al. | |
| 2022/0354710 A1 | 11/2022 | Sepello et al. | |
| 2024/0000622 A1 | 1/2024 | Stanley et al. | |
| 2024/0050288 A1 | 2/2024 | Basius | |
| 2024/0065901 A1 | 2/2024 | Stanley | |

FOREIGN PATENT DOCUMENTS

| | | | |
|---|---|---|---|
| CN | 101926709 A | 12/2010 | |
| EP | 0811362 A1 | 12/1997 | |
| EP | 1166738 A2 | 1/2002 | |
| EP | 1370161 B1 | 12/2003 | |
| EP | 2412353 A2 | 2/2012 | |
| EP | 2968030 B1 | 4/2018 | |
| JP | 4266604 B2 | 2/2009 | |
| KR | 100694187 B1 | 3/2007 | |
| WO | 2004004619 A1 | 1/2004 | |
| WO | 2013148749 A1 | 10/2013 | |
| WO | 2013186577 A1 | 12/2013 | |
| WO | 2015156686 A2 | 10/2015 | |
| WO | 2021155397 A1 | 8/2021 | |
| WO | 2022235734 A1 | 11/2022 | |

OTHER PUBLICATIONS

Anonymous, "Inkontinenzslip: hydas.de", XP093016138, Retrieved from the Internet: URL: https://web.archive.org/web/20210412055014/ https://www.hydas.de/inkontinenzslip [retrieved on Jan. 20, 2023], Apr. 12, 2021, 57 pages.

Anonymous. "Periodenpantys 2er-Pack Spitze schwarz—Secret Care", XP093016049, Retrieved from the Internet: URL: https://web.archive.org/web/20210415173928/https://www.schiesser.com/damenbekleidung-unterwaesche-slips-pants-periodenpantys-2er-pack-spitze-schwarz-secret-care.html [retrieved on Jan. 20, 2023], Apr. 15, 2021, 19 pages.

Anonymous, "Femtis—Perioden Panties—Periodenslip Ella", XP093016146, Retrieved from the Internet: URL: https://web.archive.org/web/20210726170425/https://www.femtis.de/periodenslips/perioden-slip-ella-rot.html [retrieved on Jan. 20, 2023], Jul. 26, 2021, 9 pages.

All Office Actions; U.S. Appl. No. 18/645,742, filed Apr. 25, 2024.

Unpublished U.S. Appl. No. 18/645,742, filed Apr. 25, 2024, to Jill Marlene Orr et. al.

* cited by examiner

FIT ARRAY FOR DURABLE UNDERWEAR

CROSS REFERENCE TO RELATED APPLICATION

This application claims the benefit of U.S. Provisional Application No. 63/281,108, filed Nov. 19, 2021, the substance of which is incorporated herein by reference.

BACKGROUND

Several manufacturers currently offer durable absorbent underwear pants adapted for wear and use in containing and managing menstrual discharge or light to moderate incontinent urine discharge, each manufacturer typically offering an array of sizes of underwear of a common cut style. The size arrays currently offered, however, do not reflect awareness or intent to address market preferences for combinations of secure and comfortable fit with preferred level of fit pressure for the intended wearers, over the ranges of sizes offered. To satisfy their preferences, wearers often purchase underwear having manufacturer's size designations that are not well matched to their bodies. Wearers are often required to learn, through purchase trial and error, which size designations meet their preferences, for each particular manufacturer. Opportunity remains for improvement in sizing of garments of arrays, that better and more predictably meet purchasers' sizing expectations and preferences, and reduce the need for such trial and error.

DESCRIPTION OF EXAMPLES

Definitions

Figure 1:
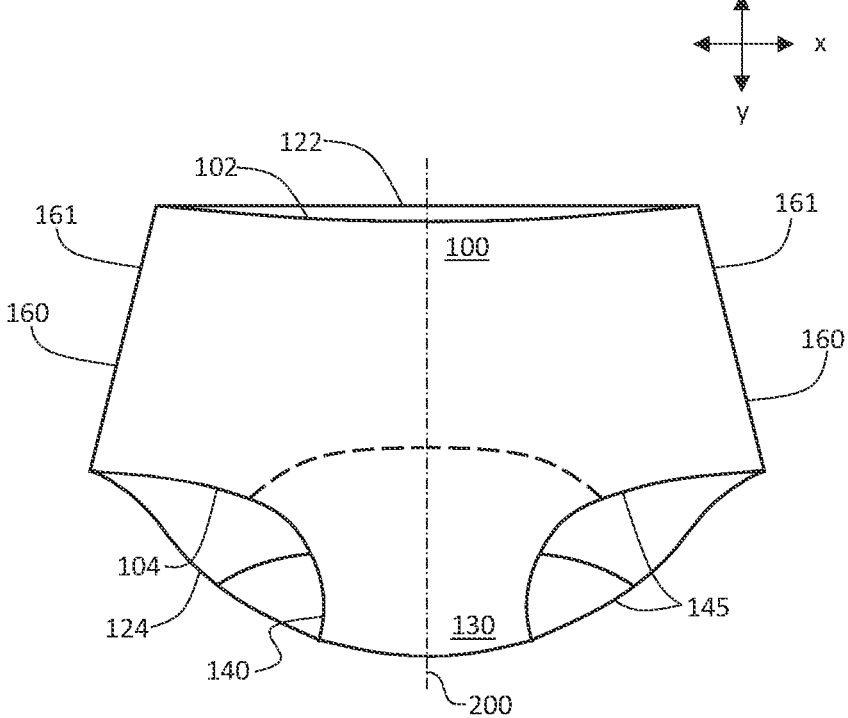
FIG. 1 is a simplified depiction of an example of a brief pant, as it would appear laid out flat on a horizontal planar surface, front waist portion facing up.

With respect to a wearable garment such as a pant, "durable" means having an outer structure made predominately of cloth material that is knitted and/or woven from natural, semi-synthetic or synthetic single- or multi-fiber thread or yarn, and which may be normally laundered or hand-washed and dried for reuse/re-wear a plurality of times without substantial loss of original shape, structure or useful mechanical attributes. A garment having an outer structure that is made predominately of nonwoven web material (composed of an accumulation of fibers or filaments that are neither knitted nor woven) and/or a polymeric film material is not deemed "durable" for purposes herein.

An "array" of products is a plurality of products of the same type marketed and/or packaged under a common trademark and/or brand name, made available contemporaneously for purchase in or through any channel.

With respect to garment products in an array of products of a common cut style designation, two "adjacently" sized products are products in the array with size designations that are closest each other, with no other products in the array having intermediate size designations sequentially between them. For example, if garment products in an array are offered as products of sequential size designations 8, 9, 10, 11, 12, 13, 14 and 15, the products of sizes 8 and 9, 9 and 10, 10 and 11, 11 and 12, etc., respectively, are "adjacently" sized, while products 8 and 10, 9 and 13, 12 and 15, etc. are not "adjacently" sized. Similarly, if garment products in an array are offered as products of sequential size designations S, M, L, XL and XXL, products of sizes S and M, M and L, L and XL, etc., respectively, are "adjacently" sized, while products of sizes S and L, M and XL, etc., are not "adjacently" sized.

A yarn, thread, fiber, filament, web, film or fabric material, or a laminate or composite of any of these, is considered to be "elastic" or "elastomeric" for purposes herein if, when a tensile force no greater than 50 gf/mm (gf per mm of sample width, where width is measured perpendicular to the stretch direction) is applied to the subject material along a stretch direction, the material may be extended along the direction to an elongated dimension of at least 130% of its original relaxed dimension (i.e., can extend at least 30%), without rupture or breakage which substantially damages the subject material; and when the force is removed from the subject material, the material retracts along the stretch direction to recover at least 40% of such elongation. To illustrate, if a section of fabric having an original relaxed length of 100 mm and a width of 40 mm can be elongated by tensile force of 2000 gf (50 gf/mm) in a direction along its length to 130 mm length without substantial damage, and will retract upon removal of the force to a length no greater than 118 mm (130 mm–118 mm=12 mm=40% of 30 mm), it is "elastic" as defined herein. "Elongation," used herein to quantify and express an amount of strain imparted to an elastic material in a stretch direction, means: {[(strained length of the strand)–(length of the strand before straining)]/ (length of the strand before straining)}, ×100%.

For a pant, the "hip size" is an actual measurement of the distance dimension of the longest lateral path present along a continuous inside surface of the pant, parallel a lateral crotch tangent line as described and depicted herein, with the fabric forming the pant along such path in a relaxed condition, but with any folds or wrinkles smoothed out.

For a pant, the "waist size" is an actual measurement of the distance of the path along the entire inside edge of the waist opening, when the waistband and/or region proximate the waist opening is in a relaxed condition, but with any folds or wrinkles smoothed out.

With respect to a pant in an opened configuration separated through the side portions (e.g., at side seams), laid out flat on a horizontal planar surface, "lateral" refers to a direction generally parallel to a line tangent each of the left and right leg opening edges where they are closest the front waist edge. With respect to a pant in an assembled configuration, laid out flat on a horizontal planar surface, front waist portion facing up, "lateral" refers to a direction generally parallel to a line tangent each of the left and right leg opening edges where they are closest the front waist edge. "Width" refers to a dimension measured along the lateral direction. Herein, the terms "x-direction" and "lateral direction" may be used interchangeably. These directions are indicated in the accompanying drawings by arrows, for purposes of illustration.

With respect to a pant in an opened configuration separated through the side portions (e.g., at side seams), laid out flat on a horizontal planar surface, "longitudinal" refers to a direction generally perpendicular to a line tangent each of the left and right leg opening edges where they are closest the front waist edge. With respect to a pant in an assembled configuration, laid out flat on a horizontal planar surface, front waist portion facing up, "longitudinal" refers to a direction generally perpendicular to a line tangent each of the left and right leg opening edges where they are closest the front waist edge. "Length" refers to a dimension measured along the longitudinal direction. Herein, the terms "y-direction" and "longitudinal direction" may be used interchangeably. These directions are indicated in the accompanying drawings by arrows, for purposes of illustration.

For purposes herein, "pant" includes any garment adapted for wear about the human lower torso, including a front waist portion and a rear waist portion that join to form side portions about the wearer's hips, and join beneath the wearer's crotch, to form a crotch portion, to form a garment having a waist opening and a pair of leg openings. Herein, the term "pant" encompasses (but is not limited to) a garment defined herein as a "brief pant"; a garment defined herein as a "legged pant", and any other garment whether adapted for use as underwear or outerwear, having such features.

"Size designation" means an indicator of relative overall size of a garment as compared to differing overall sizes of other garments of the same cut style designation offered by the same manufacturer or seller. In some examples relevant to women's underwear pants, manufacturers may use numerical size designations of sequential numbering, for example, sizes 4, 5, 6, 7, 8, 9, etc. In other examples, manufacturers may use verbal size designations, which may be abbreviated, for example, "extra small" or "XS"; "small" or "S"; "medium" or "M"; "large" or "L"; "extra large" or "XL"; "extra extra large" or "XXL" or "2XL", etc. A size designation may be associated with a garment in any suitable manner. For example, the size designation may be used in a description of the garment in advertising, marketing or other descriptive materials; it may be imprinted on a package in which the garment is offered for sale; or it may be imprinted directly on the garment, or on a tag or label attached or affixed to the garment. It will be understood that size designations are only relative, and useful for comparing and making selections from among garments of similar brand, functional type and cut style designation, and do not have a precise mathematical correlation to any particular actual dimension of a garment or any particular body measurement, given myriad potential combinations of garment types and styles, material types, material elasticity and cut styles.

"Cut style designation" refers to any verbal descriptor of a tailoring style of a garment, used by the manufacturer to inform potential purchasers of the tailoring style of the garment, for example, when the garment is not readily available for a trial donning and/or its tailoring style is not readily apparent unless the garment is actually donned. In the context of women's underwear pants, non-limiting, illustrative examples include "hipster"; "hip hugger"; "bikini"; "high waist"; "boy short"; etc.

With respect to two opposing surfaces of a layer component of a pant, or combination of layer components, "wearer-facing" refers to the surface that faces the wearer's skin when the pant is worn normally; and "outward-facing" refers to the surface that faces away from the wearer's skin. With respect to two distinct layered components of a pant, the "wearer-facing" component is the component that is disposed closest the wearer's skin when the pant is worn normally; and the "outward-facing" component is the component that is disposed farthest from the wearer's skin.

With respect to a pant in an opened configuration separated through the side portions (e.g., at side seams), laid out flat on a horizontal planar surface occupying an x-y plane, the "z-direction" is the direction orthogonal to the x-y plane, i.e., the vertical direction relative the horizontal planar surface.

For purposes herein, "pant" includes any garment adapted for wear about the human lower torso, including a front waist portion and a rear waist portion that join about the wearer's hips and beneath the wearer's crotch, to form a garment having a waist opening and a pair of leg openings. Herein, the term "pant" encompasses (but is not limited to) a garment defined herein as a "brief pant"; a garment defined herein as a "legged pant", and any other garment whether adapted for use as underwear or outerwear, having such features.

For purposes herein, unless otherwise specified, with respect to the proportionate content of a component material in a composition or structure, "predominate" means the component constitutes the majority of the weight of the composition or structure.

Figure 4:
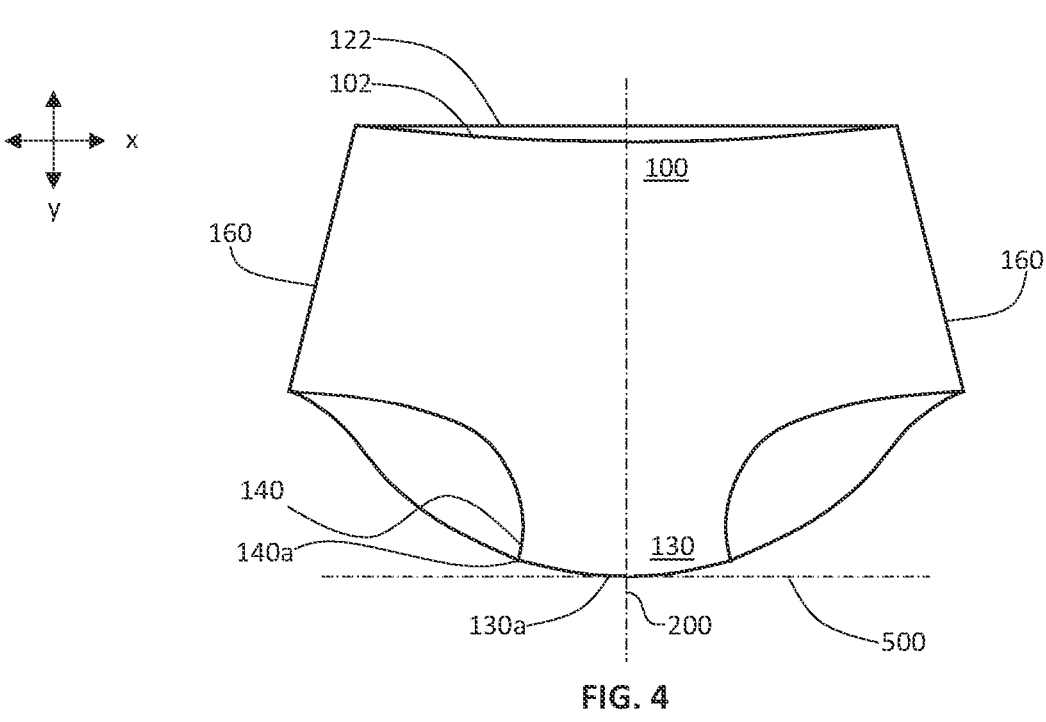
FIG. 4 is a simplified depiction of another example of a brief pant, as it would appear laid out flat on a horizontal planar surface, front waist portion facing up.
Figure 5:
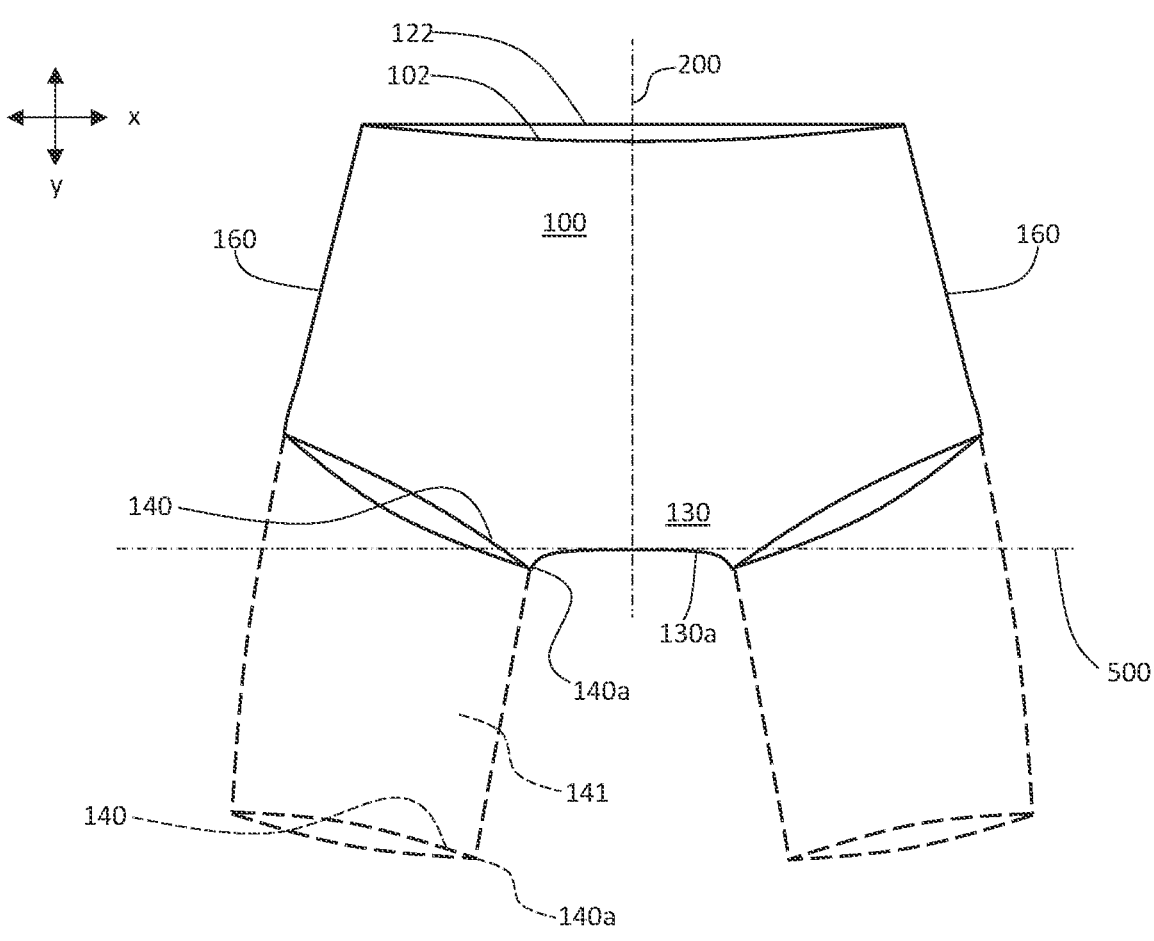
FIG. 5 is a simplified depiction of an example of a legged pant, as it would appear laid out flat on a horizontal planar surface, front waist portion facing up.

For purposes herein, a "brief pant" is distinguished from a "legged pant" by the configuration of the inside leg edges, resulting from the manner in which the component materials are shaped, sized, proportioned and seamed or otherwise affixed together. FIG. 4 depicts an example of a brief pant and FIG. 5 depicts an example of a legged pant in alternative forms. When the garment in its assembled condition is laid out flat on a horizontal planar surface, front waist portion facing up, and a lateral crotch tangent line 500 is drawn perpendicularly to longitudinal axis 200 and tangent to the point at which the crotch portion lower profile 130a intersects the longitudinal axis 200, for a brief pant, the lowermost points 140a along the inside leg opening edges 140 are disposed along or above the crotch tangent line 500 (i.e., toward the front waist edge 102) (see FIG. 4); and for a legged pant, the lowermost points 140a along the inside leg opening edges 140 are disposed below the crotch tangent line 500 (i.e., away from the front waist edge 102) (see FIG. 5).

General Pant Features

Generally, the underwear pants contemplated herein may have any features ordinarily associated with durable underwear pants, including underwear pants with added absorbency features for use in managing fluid discharges that accompany menstruation and incontinence.

The underwear pants may include any features described in, by way of non-limiting example, US 2021/0290447 and U.S. App. Ser. No. 63/184,839.

For underwear, some women prefer brief pants rather than legged pants such as "boy shorts" styles for ordinary daily wear. Depending upon individualized body contours and personal preferences, this may be due to issues of comfort; unlike a legged, shorts-type pant, a brief pant ordinarily might not ride up and bunch about the legs from changes of body position, and thereby be a source of unwanted concentration of material bulk, tightness about the legs or other discomfort under outer clothing. Further, due to the manner in which their leg edges tend to cause the pant to fit through the crotch region of the body, brief pants having suitable elastic stretch characteristics may be preferred for maintaining a close fit about the female genital/urethra area, for purposes of protecting against leakage of body fluids such as menstrual fluid or unintended discharges of urine. On the other hand, some women may prefer legged pant styles for ordinary daily wear. Again, this will depend upon individualized body contours and personal preferences, and issues of comfort. Legged pant styles may be configured with appropriate tailoring and stretch features to closely conform to the wearer's body through the crotch region, and still enable projection against leakage of body fluids. Arrays of brief pants and arrays of legged pants are contemplated herein.

Referring to FIGS. 1-5 as illustrative but non-limiting examples, a pant may include a front waist portion 100, a rear waist portion 120 and a crotch portion 130 bridging the front and rear waist portions. Front waist portion 100 has a front waist edge 102, and left and right front leg opening edges 104. Rear waist portion 120 has a rear waist edge 122, and left and right rear leg opening edges 124. Crotch portion 130 has left and right crotch leg opening edges 140.

Figure 3:
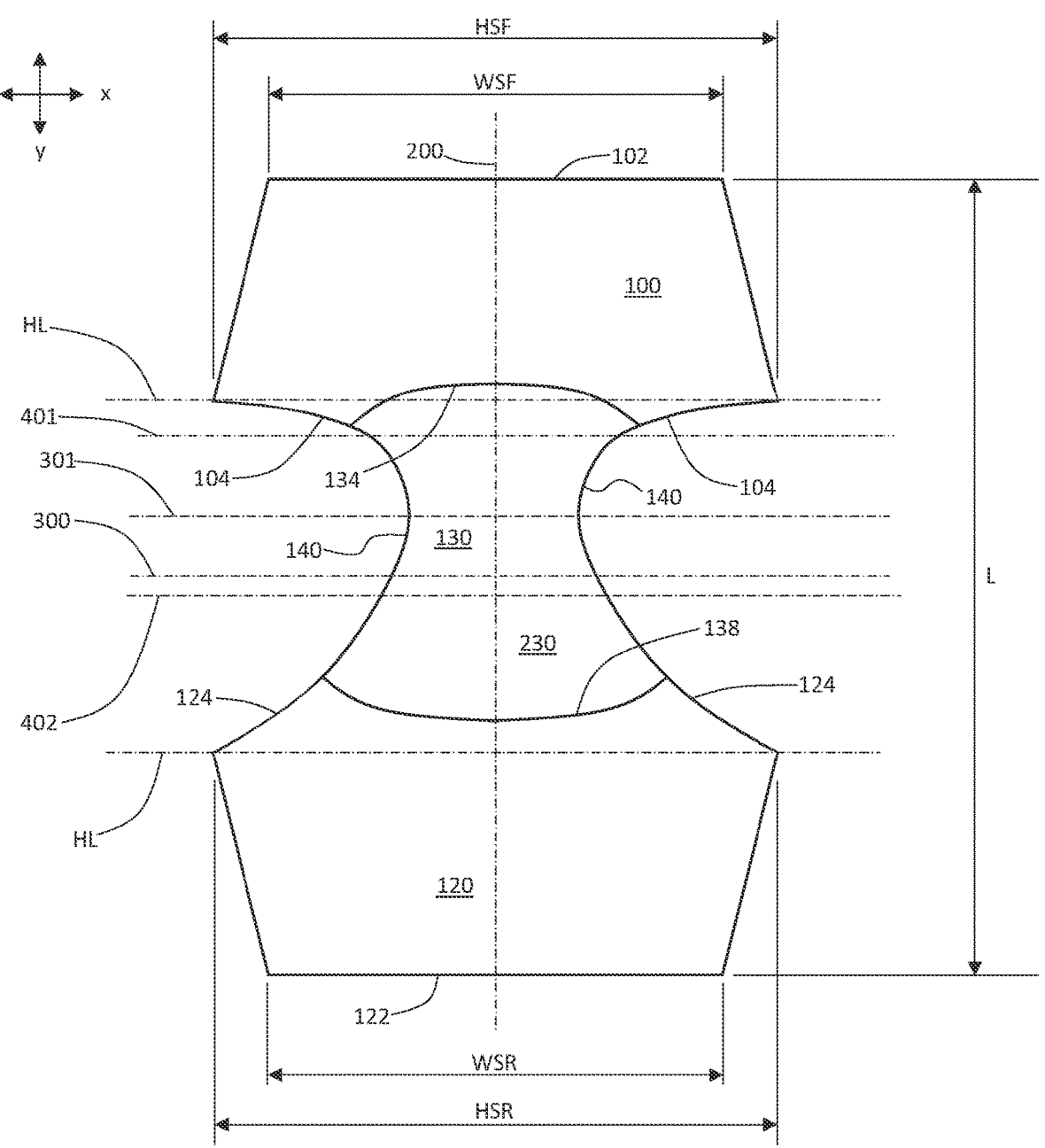
FIG. 3 is a depiction of one example of a brief pant such as the one shown in FIG. 1, in an opened configuration wherein the front and rear waist portions have been separated at the hip portions or hip side seams, as it would appear laid out flat on a horizontal planar surface, wearer-facing surfaces facing up.

Crotch portion 130 may include or consist of a crotch gusset 230 that may include one or more layer components added to the inside of the pant at least in the crotch portion, included for purposes of adding or enhancing fluid absorbency. (For purposes herein, the "crotch portion 130" is a portion of a pant identified as described herein, independently of specific components or structures. A "crotch gusset 230" is structural component that may include at one or more added, distinct layers that may bridge the front waist portion 100 and the rear waist portion 120. Referring to FIG. 3, for purposes herein, crotch portion 130 is the portion of the pant, at a minimum, lying between crotch portion minimum front extent 401 and crotch portion minimum rear extent 402, longitudinally centered about crotch portion lateral axis 301. Crotch lateral axis 301 is drawn along the smallest measurable width dimension between the crotch leg opening edges 140. Crotch portion front extent 401 and rear extent 402 are parallel to crotch portion lateral axis 301 and are each located at 10 percent of the overall length L of the pant respectively to the front and the rear of crotch portion lateral axis 301. As suggested by FIG. 3, it may be desired that the crotch portion lateral axis 301 be disposed forward of the lateral axis 300 (which equally divides overall length L), rather than be co-located with lateral axis 300, for purposes of better fit about an adult female wearer's legs and lower torso. Thus, the respective boundaries between crotch portion 130 and front and rear waist portions 100, 120 for purposes herein are independent of the location(s) of any seams such as seams 134, 138 that may be present to join material(s) included in the crotch gusset 230 and material(s) included in the front and rear waist portions 100, 120.

Material(s) forming crotch portion 130 may be continuous with material(s) forming front and rear waist portions 100, 120, or alternatively, one or both of forward and rearward portions of the crotch portion 130 and/or crotch gusset 230 may be substantially formed of one or more sections or layers of material that are distinct from material(s) substantially forming one or both of front and rear waist portions 100, 120. Crotch gusset 230 may be joined to front and rear waist portions 100, 120 at one or both of forward seam 134 and rearward seam 138. In illustrative but non-limiting examples reflected in FIGS. 1 and 2, front waist portion 100, an outward-facing layer of crotch portion 130, and rear waist portion 120, may be formed partially or entirely of a first single, continuous section of material. In the examples shown, one or more additional layers of material may be added to crotch portion 130 on the wearer-facing side as shown, and be affixed to the first section of material via, e.g., stitching/sewing, adhesive bonding, thermal bonding (fusing or welding) or other suitable attachment/joining mechanism (hereinafter, attachment mechanism) at forward and rearward seams 134, 138, and/or along the leg edges including inside leg opening edges 140, thereby forming a crotch gusset 230.

In other illustrative but non-limiting examples (not specifically shown), the sections of materials respectively forming front waist portion 100, rear waist portion 120 and crotch gusset 230 may be separate and distinct, and joined via any suitable attachment mechanism at forward and rearward seams 134, 138.

Figure 2:
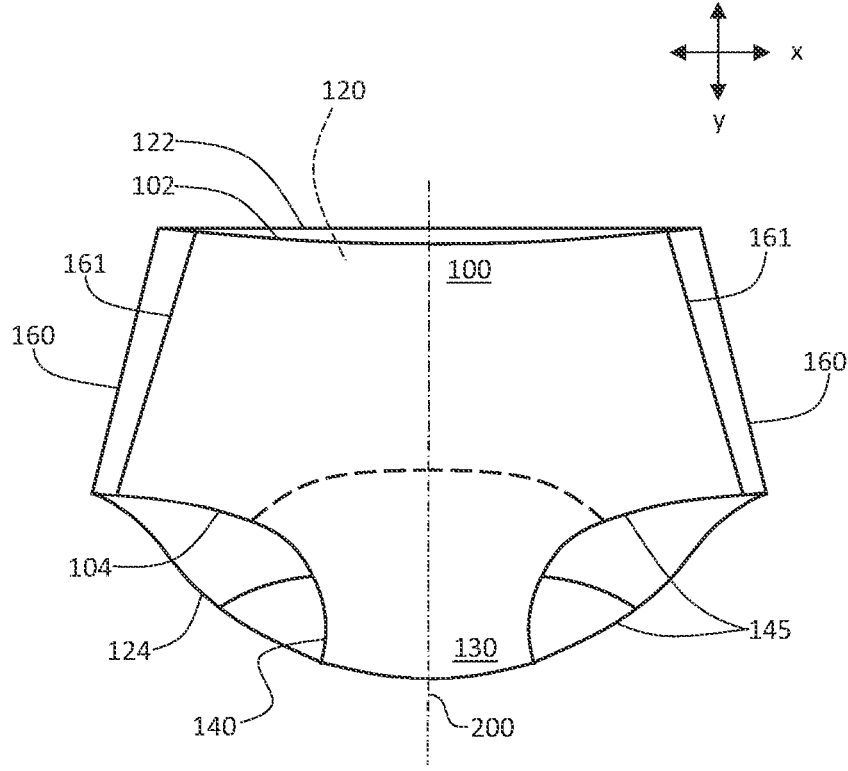
FIG. 2 is a simplified depiction of another example of a brief pant, as it would appear laid out flat on a horizontal planar surface, front waist portion facing up.

Hip side portions 160 may include side seams 161, at which the front waist portion 100 and rear waist portion 120 are joined together in the fully assembled pant. In some examples the front waist portion 100 and rear waist portion 120 will be of substantially equal lateral dimensions or widths, resulting in the disposition of side seams 161 at the laterally outermost portions at the hip side portions 160, as suggested in FIG. 1. In other examples, the front waist portion 100 and rear waist portion 120 may be of differing lateral dimensions or widths (as may be appreciated when the pant structure is opened at the side seams and laid out flat), resulting in the disposition of side seams 161 forward or rearward of the laterally outermost portions of the hip side portions 160. For example, as shown in FIG. 2, the rear waist portion 120 may be wider along, e.g., rear waist edge 122, than front waist portion 100 and front waist edge 102. As a result, side seams 161 are disposed forward of the laterally outermost portions of hip side portions 160.

Materials Selection

Generally, the front and rear waist portions 100, 120 of suitable examples of a pant may be formed of any fabric material or combination of fabric and other materials known and used as components of underwear, swimwear or athletic/active wear, exhibiting suitable attributes that may include, depending upon the location of the fabric within the structure, pleasing feel against the skin (softness and/or low-friction/smooth/silky feel), low caliper/bulk, elongation capability, elasticity, absorbency, wicking ability, breathability, etc.

Crotch portion 130 and/or crotch gusset 230, in some examples requiring absorbency and longitudinal elastic stretch attributes, may include a combination of several materials selected to impart the structure with the desired attributes.

Fabric Structure

Most durable fabrics exhibit anisotropic elongation capabilities. Generally, it may be desired that materials included to form the front waist portion 100, rear waist portion 120, crotch portion 130 and crotch gusset 230 be one or more knitted fabrics.

The constituent yarns or threads of knitted fabrics do not follow straight paths along the plane of the fabric, and are neither parallel nor perpendicular to each other. Rather, each constituent yarn or thread of a knitted fabric follows a looping path along successive rows, interlooping with one or more constituent yarns or threads in adjacent rows. As a result, knitted fabrics generally exhibit elongation capability along all directions, even where the constituent yarns or threads themselves are not elastic. For this reason, unless a woven fabric is desired for a particular reason, it may be preferred that a knitted fabric be used to form any one or more, or all, of the fabric layers included to form the pant.

Even so, most types of knitted fabrics have elongation capabilities that are anisotropic along the plane of the fabric, having a first direction of greatest elongation capability and a second direction, perpendicular to the first direction, of least elongation capability. Accordingly, when knitted fabric is selected and used to form waist portions of the pant 100, 120, it may be desired that the fabric(s) forming those portions be oriented such that their directions of greatest elongation capability are at least approximately parallel with the lateral direction of the pant. This may be desired because underwear pants are typically required to stretch most in the lateral direction, when being donned and worn. In some examples, however, such as when the pant is an absorbent pant designed for management of bodily fluid discharges (menstrual fluid or urine), it may be desired that knitted fabric material(s) forming one or more layers in the crotch portion 130, for examples, materials forming a crotch gusset 230, be oriented so as to have their direction of greatest elongation/stretch capability at least approximately parallel with the longitudinal direction, as discussed in US 2021/0290447.

Arrays

Manufacturers of underwear pants often offer their products in several cut styles, in accompaniment with cut style designations. For example, a manufacturer may offer underwear products designated as "hipster" style, "bikini" style, "high waist" or "full coverage" style, "boy short" style, etc. These designations are generally intended to be suggestive or descriptive of the tailoring styles of the products, which may not be readily apparent to the wearer until they are actually removed from the retail packaging, and donned.

Manufacturers also typically offer arrays of pants of each cut style they make, of a number of sizes. The manufacturer will assign each size in the array a size designation. Examples of size designations commonly used include verbal descriptors and abbreviations thereof, like "extra small" or "XS"; "small" or "S"; "medium" or "M"; "large" or "L", "extra large" or "XL", "double extra large" or "XXL" or "2XL", etc. Other examples of size designations include standard numerical size designations, e.g., sizes 4, 5, 6, 7, 8, 9, 10, 11, 12, 13,14, etc.

There are accepted, although not necessarily universal or standardized, published charts correlating commonly-used size designations and, for example, intended wearer waist and/or hip measurements. For example, the following correlations are currently published by a US garment industry source, for the US market:

| Numerical Size Designation (US) | Verbal Size Designation (abbreviation) | Intended Wearer Waist Measurement (inches) | Intended Wearer Hip Measurement (inches) |
|---|---|---|---|
| 2 | XXS | 21-22 | 27-29 |
| 3 | XS | 23-24 | 30-32 |
| 4 | S | 25-26 | 33-35 |
| 5 | M | 27-28 | 36-38 |
| 6 | L | 29-31 | 39-41 |
| 7 | XL | 32-34 | 42-44 |
| 8 | XXL | 35-37 | 45-47 |
| 9 | 3XL | 38-41 | 48-50 |
| 10 | 4XL | 42-44 | 51-53 |
| 11 | 5XL | 45-47 | 54-56 |

(See http://sizechart.com/panties/us/index.html.)

While such sizing correlation charts are sometimes used by manufacturers of women's underwear for purposes of sizing products for arrays of products of a common cut style designation, they are not standardized or universal. Further, manufacturers often deviate from these, or rely on alternative sizing correlation charts. Manufacturers are also not necessarily consistent with each other in the uses of sizing designations. Adding complexity, there are myriad cut styles available, and imaginable, and permutations of combinations thereof, with a large variety of suitable fabrics (having, e.g., varying stretch characteristics) that impact garment sizing and correlation with intended wearer measurements.

Through research in connection with fit preferences of adult female wearers/users of absorbent underwear for managing incontinence, two general preference trends in the market have been discovered that, it is believed, have not been previously recognized by manufacturers and sellers of underwear for women, or at least manufacturers of absorbent underwear for managing menstrual discharge and/or incontinence. In this research, it has been discovered that (1) as wearers grow larger in their body measurements, they tend to prefer underwear that fits more snugly, i.e., exerts comparatively greater pressure inwardly against the body ("normal pressure"), during wear; and (2) as wearers grow larger in their body measurements, they tend to prefer underwear in which the ratio between hip size and waist size of the underwear (measured as described below) decreases.

Following discovery of these general preferences, it has been further discovered that sizing underwear pants constituting an array, of a particular cut style designation, in a manner consistent with these preferences, results in greater wearer satisfaction with purchase decisions based on the manufacturer's size designations, and with the wearers' perceptions of satisfactory fit of the purchased pant product.

To illustrate, using the correlation chart above a first wearer of relatively smaller body measurements may purchase an underwear pant product having a size designation of, e.g., "small". A product having that size designation will be sized by the manufacturer in a manner believed to result in a properly- and comfortably-fitting garment for a wearer having the published, intended hip measurements as set forth in the chart above, i.e., 33-35 inches, or an average of 34 inches. Using a fabric that has elastic stretch properties to make the waist portions of the pant, the manufacturer may size the pant to have a pant hip size smaller than the intended wearer hip measurement, assuming, e.g., that the fabric will be required to stretch laterally 50 percent beyond its relaxed size, upon donning and wear. Thus, the manufacturer may choose to size the pant with a hip size of 22.7 inches (34 inches/150 percent). To make a larger size pant of the same cut style designation, the same manufacturer, using the same fabric, may simply decide to increase the pant hip size dimension in direct accordance with the increase of intended wearer hip measurement in the published correlations. Thus, for a second wearer having relatively larger body measurements, e.g., hip measurement of 45-47 inches, the manufacturer may offer the product with an "XXL" size designation, and size the product as 22.7 inches+(46 inches–34 inches) =34.7 inches.

It will be noted, however, that such a sizing choice by the manufacturer for the larger size pant can result in a more loosely-fitting pant about the hips of the larger intended wearer—because less fabric stretch per unit unstretched dimension will be required of the larger pant to fit the intended wearer, than of the smaller pant: While the smaller pant will be required to stretch laterally by 50 percent (as assumed), the larger pant will only be required to stretch laterally by [(46 inches–34.7 inches)/34.7 inches]×100 percent=32.6 percent. This will result in a more loosely-fitting pant, which exerts less normal pressure on the wearer's body, than the smaller pant. Such an approach would not recognize the wearer market preference identified herein.

From measurements taken of products of two differing arrays of underwear pants currently offered by one manufacturer, it has been observed that these products do not reflect observance of the wearer market preference identified herein, and further, that such arrays appear to have pant size increases associated with size designation steps upward, that seem not to have been determined in a consistent manner. Samples of arrays of SPEAX absorbent underwear (Thinx, Inc., New York, N.Y., USA) in two cut style designations, "Hi-Waist" and "Hiphugger", were obtained and measured. Tables 1A, 1B, 2A and 2B below reflect the size designation data provided by the manufacturer, the measured hip and waist sizes recorded, and calculated figures including normal pressure as indicated and the ratio of hip size to waist size. Normal pressure was calculated based on measured total lateral tensile force at the hip size measurement locations, based on an assumption of a cylindrical body shape having a circumference equal to the intended wearer hip measurement, at an applied strain amount sufficient to laterally stretch the pant to a hip dimension equal to the intended wearer hip measurement.

TABLE 1A

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Speax Hi-Waist | XS | 851 | 561 | | | 0.055 |
| | S | 902 | 597 | 36 | 106.3% | 0.051 |
| | M | 953 | 613 | 16 | 102.7% | 0.055 |
| | L | 1003 | 668 | 55 | 109.0% | 0.044 |
| | XL | 1054 | 720 | 52 | 107.7% | 0.037 |
| | 2XL | 1105 | 795 | 75 | 110.4% | 0.025 |
| | 3XL | 1156 | 800 | 5 | 100.7% | 0.031 |
| | 4XL | 1207 | 882 | 82 | 110.3% | 0.021 |
| | 5XL | 1257 | 894 | 12 | 101.3% | 0.024 |

TABLE 1B

| Product Array | Verbal size design. (abbrev.) | Intended wearer hip meas. (mm) | Pant waist size (mm) | Waist size increase (mm) | Pant waist size increase % | Pant hip size to waist size difference (mm) | Pant Hip Size to Waist Size Ratio |
|---|---|---|---|---|---|---|---|
| Speax Hi-Waist | XS | 851 | 455 | | | 106 | 1.23 |
| | S | 902 | 493 | 38 | 108.3% | 104 | 1.21 |
| | M | 953 | 494 | 1 | 100.3% | 119 | 1.24 |
| | L | 1003 | 537 | 43 | 108.7% | 131 | 1.24 |
| | XL | 1054 | 592 | 56 | 110.4% | 127 | 1.22 |
| | 2XL | 1105 | 680 | 88 | 114.8% | 114 | 1.17 |
| | 3XL | 1156 | 681 | 1 | 100.1% | 119 | 1.18 |
| | 4XL | 1207 | 768 | 87 | 112.7% | 114 | 1.15 |
| | 5XL | 1257 | 768 | 0 | 100.0% | 126 | 1.16 |

TABLE 2A

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Speax Hiphugger | XS | 851 | 601 | | | 0.045 |
| | S | 902 | 651 | 50 | 108.2% | 0.038 |
| | M | 953 | 701 | 50 | 107.7% | 0.031 |
| | L | 1003 | 727 | 26 | 103.7% | 0.033 |

TABLE 2A-continued

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| | XL | 1054 | 756 | 29 | 104.0% | 0.034 |
| | 2XL | 1105 | 784 | 28 | 103.7% | 0.034 |
| | 3XL | 1156 | 798 | 14 | 101.8% | 0.038 |
| | 4XL | 1207 | 854 | 56 | 107.0% | 0.032 |
| | 5XL | 1257 | 897 | 43 | 105.1% | 0.029 |

TABLE 2B

| Product Array | Verbal size design. (abbrev.) | Intended wearer hip meas. (mm) | Pant waist size (mm) | Waist size increase (mm) | Pant waist size increase % | Pant hip size to waist size difference (mm) | Pant Hip Size to Waist Size Ratio |
|---|---|---|---|---|---|---|---|
| Speax | XS | 851 | 557 | | | 45 | 1.08 |
| Hiphugger | S | 902 | 582 | 25 | 104.5% | 69 | 1.12 |
| | M | 953 | 605 | 23 | 104.0% | 96 | 1.16 |
| | L | 1003 | 609 | 4 | 100.6% | 118 | 1.19 |
| | XL | 1054 | 656 | 47 | 107.8% | 100 | 1.15 |
| | 2XL | 1105 | 720 | 64 | 109.8% | 64 | 1.09 |
| | 3XL | 1156 | 732 | 12 | 101.6% | 67 | 1.09 |
| | 4XL | 1207 | 798 | 66 | 109.0% | 56 | 1.07 |
| | 5XL | 1257 | 833 | 36 | 104.5% | 64 | 1.08 |

From the data above, it can be seen that the examples of SPEAX underwear pants measured did not exhibit consistent or uniform increases or decreases in hip or waist size, with steps up in size designation. Rather, the hip and waist size data above indicates inconsistencies in increases and decreases of upward sizing increments, with upward step changes in size designations.

Further, from calculations of normal pressure based on measured lateral tensile forces and applied strain at the pant hip size measurement locations (identified as described below) (assuming a cylindrical body shape with a circumference equal to the intended wearer hip measurement), the pants studied did not exhibit consistency or uniform increases in normal pressure, with upward step changes in size designation. Rather, the calculated pressure data shown above indicates several decreases in normal pressure associated with several upward step changes in size designations, among pants in the arrays.

Such array sizing does not reflect awareness of the discovery, identified herein, that as wearers' body measurements increase, their preferences shift toward relatively more snugly-fitting underpants. Assuming that first and second wearers in the illustration set forth above were making their selections according to the published sizing correlation and their actual body measurements, the larger-measurement wearer would experience a product that fits more loosely than the product purchased by the smaller-measurement wearer, and might be dissatisfied as a result. Through purchase trial-and-error the larger-measurement wearer then may identify and select a product having a size designation smaller than what is indicated by the manufacturer for her body measurements, to obtain a more snugly-fitting product. The trial-and-error that the larger-measurement wearer must undergo to identify a product with satisfactory fit is not deemed an efficient or desirable situation for satisfying purchaser-wearer expectations. A further risk to the manufacturer/seller is that the purchaser-wearer may simply conclude that the particular product/brand does not fit properly or according to her preferences, and then move on to shop competitor's products.

It has been learned that an array of underwear pants of a common cut style designation (and fabric constitution) may be sized in a manner such that their hip sizes (with fabric in a relaxed condition), are not increased in direct 1:1 proportion to the increase in intended wearer hip measurements, and thereby, can be sized within the array to result in consistent or increasing normal pressure for the wearer, with upward steps in pant size designations. Without intending to be bound by theory, it is believed that such sizing scheme for underwear pants in an array of any particular cut style designation will reduce wearer effort and potential frustration with underwear product size selection, and thereby promote greater purchaser-wearer satisfaction.

Accordingly, in any array of underwear pants of a common cut style designation having, e.g., five differing, sequentially adjacent size designations, in which:

a pant of a first size designation S1 has a first pant hip size HS1, a pant of a second size designation S2 has a second pant hip size HS2, a pant of a third size designation S3 has a third pant hip size HS3, a pant of a fourth size designation S4 has a fourth pant hip size HS4, and a pant of a fifth size designation S5 has a fifth pant hip size HS5, the manufacturer may desire to size the pants in the array such that for any plurality of pants of sequentially adjacent size designations in the array, the pant hip sizes have the following relationship, or for any plurality of adjacent size designations fewer than five in number, a subpart thereof:

$$(HS2-HS1) \geq (HS3-HS2) \geq (HS4-HS3) \geq (HS5-HS4).$$

In addition, or in the alternative, the manufacturer may desire to size the pants in the array such that for any plurality of pants of sequentially adjacent size designations in the array, the pant hip sizes have the following relationship, or for any plurality of adjacent size designations fewer than five in number, a subpart thereof:

$$[(HS2-HS1)/HS1] \geq [(HS3-HS2)/HS2] \geq [(HS4-HS3)/HS3] \geq [(HS5-HS4)]/HS4].$$

Figure 9:
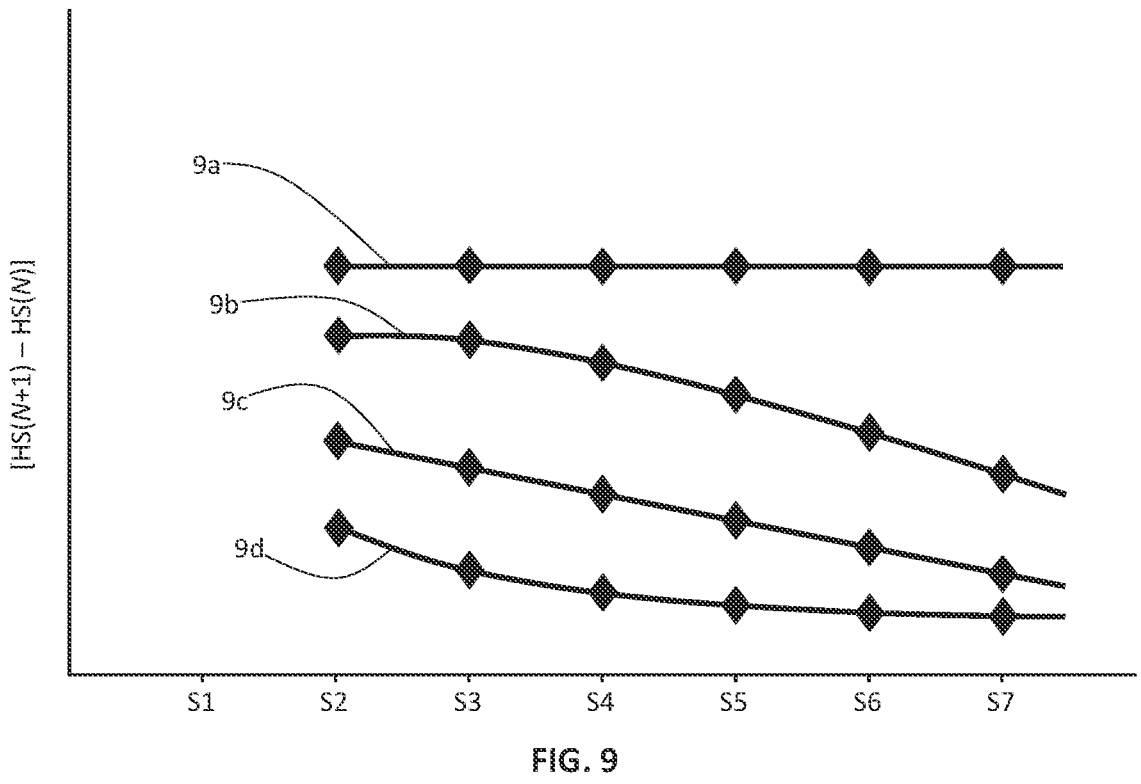
FIG. 9 is a schematic illustration of various possible plots of differences in hip size change [HS(N+1)-HS(N)] versus pant size designations as contemplated herein.

Expressed verbally, these relationships mean, generally, that as the manufacturer's size designations for pants in an array of a particular cut style designation go up sequentially, the associated upward steps in actual pant hip sizes in the array are either equal, or decrease. Various possible conceptual examples of this relationship are illustrated in FIG. 9. Plot 9a represents a sizing scheme in which each size designation in the array (from S2 up) involves an equal increase in pant hip size, over the increase of pant hip size associated the adjacent lower size designation. Plots 9b-9d represent sizing schemes in which each size designation in the array (from S2 up) involves an increase in pant hip size that is less than the increase in hip size associated with the adjacent lower designation. Without intending to be bound by theory, it is believed that such sizing scheme becomes particularly important to the wearer market for arrays or subparts of arrays of relatively larger sizes, e.g., actual pant hip sizes equal to or greater than 760 mm.

For arrays of underwear pants having more than five differing and distinct size designations, the mathematical relationships set forth above may be continued with each additional size designation (S6, S7, and so on), e.g., $$(HS5-HS4) \geq (HS6-HS5) \geq (HS7-HS6), \text{ and so on,} \text{ and}$$

$$[(HS5-HS4)/HS4] \geq [(HS6-HS5)]/HS5] \geq [(HS7-HS6)]/HS6], \text{ and so on.}$$

With respect to underwear pants that are intended/designed to be used to contain and/or absorb discharges of fluid resulting from menstruation or incontinence, it should be noted that the consistency or increase in normal pressure against the wearer's body with increasing size designation, resulting from sizing according to this sizing scheme, can help provide an array of underwear pants that more effectively and consistently conform to wearer's bodies so as to hold absorbent components thereof against wearer's bodies, throughout the range of size designations in the array—particularly when the absorbent components are weighed down and/or made bulkier with absorbed fluid. In this regard, when array features herein are combined with longitudinal stretch features of underwear pants described in US 2021/0290447, further synergistic body conformance benefits can result.

In a manner similar to increasing pant hip size in association with upward steps in designated size according to a sizing scheme as described above, pant waist sizes also may be increased in association with designated sizes such that they observe the discovery described herein. Accordingly, in any array of underwear pants of a common cut style designation having, e.g., five differing and distinct size designations in the array, in which:

a pant of a first size designation S1 has a first pant waist size WS1, a pant of a second size designation S2 has a second pant waist size WS2, a pant of a third size designation S3 has a third pant waist WS3, a pant of a fourth size designation S4 has a fourth pant waist size WS4, and a pant of a fifth size designation S5 has a fifth pant waist size WS5, the manufacturer may desire to size the pants in the array such that for any plurality of pants of sequentially adjacent size designations in the array, the pant waist sizes have the following relationship, or for any plurality of adjacent size designations fewer than five in number, an associated subpart thereof:

$$(WS2-S1) \geq (WS3-S2) \geq (WS4-S3) \geq (WS5-S4).$$

In addition, or in the alternative, the manufacturer may desire to size the pants in the array such that for any plurality of pants of sequentially adjacent size designations, the pant hip sizes have the following relationship, or for any plurality of adjacent size designations fewer than five in number, an associated subpart thereof:

$$[(WS2-S1)/WS1] \geq [(WS3-S2)/WS2] \geq [(WS4-S3)/WS3] \geq [(WS5-S4)]/WS4].$$

Expressed verbally, these relationships mean, generally, that as the manufacturer's size designations for pants in an array of a particular cut style designation go up sequentially, the corresponding upward steps in actual pant waist sizes in the array are either equal, or decrease.

For arrays of underwear pants having more than five differing and distinct size designations in the array, the mathematical relationships set forth above may be continued with each additional size designation (S6, S7, and so on), e.g., $$(WS5-S4) \geq (WS6-S5) \geq (WS7-S6), \text{ and so on, and}$$

$$[(WS5-S4)/WS4] \geq [(WS6-S5)]/WS5] \geq [(WS7-S6)]/WS6], \text{ and so on.}$$

For purposes of experimentation and discovery, prototype underwear pants constituting respective potential arrays of two differing cut styles were manufactured to particular size specifications. The component material used for the prototypes was a knitted fabric of 76 percent nylon and 24 percent Lycra Spandex, obtained from IKAR Ltd. (Raanana, Israel and New York, N.Y., USA). In each of the pants, the direction of greatest elongation of the fabric was oriented at least approximately parallel to the lateral direction thereof. Hip sizes and waist sizes for each pant were measured, and estimates of the normal pressure they would apply to a wearer were calculated as described above. Tables 3A through 6A below contain the measured and calculated data:

TABLE 3A

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Prototype | XS | 851 | 653 | | | 0.035 |
| Array 1 | S | 902 | 686 | 33 | 105.1% | 0.035 |
| High Waist | M | 953 | 719 | 33 | 104.8% | 0.035 |
| Brief | L | 1003 | 751 | 32 | 104.5% | 0.035 |

TABLE 3A-continued

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Uniform | XL | 1054 | 783 | 32 | 104.3% | 0.035 |
| Pressure by | 2XL | 1105 | 815 | 32 | 104.0% | 0.035 |
| Size | 3XL | 1156 | 846 | 31 | 103.8% | 0.035 |
| | 4XL | 1207 | 877 | 31 | 103.6% | 0.035 |
| | 5XL | 1257 | 908 | 31 | 103.5% | 0.035 |

TABLE 3B

| Product Array | Verbal size design. (abbrev.) | Intended wearer hip meas. (mm) | Pant waist size (mm) | Waist size increase (mm) | Pant waist size increase % | Pant hip size to waist size difference (mm) | Pant Hip Size to Waist Size Ratio |
|---|---|---|---|---|---|---|---|
| Prototype | XS | 851 | 522 | | | 131 | 1.25 |
| Array 1 | S | 902 | 557 | 35 | 106.7% | 129 | 1.23 |
| High Waist | M | 953 | 593 | 36 | 106.4% | 126 | 1.21 |
| Brief | L | 1003 | 629 | 36 | 106.2% | 122 | 1.19 |
| Decreasing | XL | 1054 | 667 | 37 | 105.9% | 117 | 1.18 |
| Hip Size/ | 2XL | 1105 | 705 | 38 | 105.7% | 110 | 1.16 |
| Waist Size | 3XL | 1156 | 744 | 39 | 105.5% | 102 | 1.14 |
| Ratio with | 4XL | 1207 | 784 | 40 | 105.4% | 93 | 1.12 |
| Increasing | 5XL | 1257 | 825 | 41 | 105.2% | 83 | 1.10 |
| Size Desig. | | | | | | | |

TABLE 4A

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Prototype | XS | 851 | 662 | | | 0.032 |
| Array 2 | S | 902 | 690 | 28 | 104.3% | 0.034 |
| High Waist | M | 953 | 717 | 27 | 103.9% | 0.036 |
| Brief | L | 1003 | 742 | 25 | 103.5% | 0.038 |
| Increasing | XL | 1054 | 766 | 24 | 103.2% | 0.040 |
| Pressure by | 2XL | 1105 | 788 | 22 | 102.9% | 0.043 |
| Size | 3XL | 1156 | 809 | 21 | 102.6% | 0.045 |
| | 4XL | 1207 | 828 | 19 | 102.3% | 0.048 |
| | 5XL | 1257 | 844 | 17 | 102.0% | 0.051 |

TABLE 4B

| Product Array | Verbal size design. (abbrev.) | Intended wearer hip meas. (mm) | Pant waist size (mm) | Waist size increase (mm) | Pant waist size increase % | Pant hip size to waist size difference (mm) | Pant Hip Size to Waist Size Ratio |
|---|---|---|---|---|---|---|---|
| Prototype | XS | 851 | 529 | | | 132 | 1.25 |
| Array 2 | S | 902 | 560 | 31 | 105.9% | 130 | 1.23 |
| High Waist | M | 953 | 591 | 31 | 105.5% | 126 | 1.21 |
| Brief | L | 1003 | 622 | 31 | 105.2% | 120 | 1.19 |
| Decreasing | XL | 1054 | 652 | 30 | 104.9% | 114 | 1.18 |
| Hip Size/ | 2XL | 1105 | 682 | 30 | 104.6% | 107 | 1.16 |
| Waist Size | 3XL | 1156 | 711 | 29 | 104.3% | 98 | 1.14 |
| Ratio with | 4XL | 1207 | 740 | 29 | 104.0% | 88 | 1.12 |
| Increasing | 5XL | 1257 | 768 | 28 | 103.8% | 77 | 1.10 |
| Size Desig. | | | | | | | |

TABLE 5A

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Prototype | XS | 851 | 680 | | | 0.035 |
| Array 3 | S | 902 | 715 | 35 | 105.2% | 0.035 |
| Hipster | M | 953 | 750 | 35 | 104.9% | 0.035 |
| Uniform | L | 1003 | 784 | 34 | 104.6% | 0.035 |
| Pressure by | XL | 1054 | 818 | 34 | 104.3% | 0.035 |
| Size | 2XL | 1105 | 851 | 33 | 104.1% | 0.035 |
| | 3XL | 1156 | 884 | 33 | 103.9% | 0.035 |
| | 4XL | 1207 | 917 | 33 | 103.7% | 0.035 |
| | 5XL | 1257 | 950 | 32 | 103.5% | 0.035 |

15

TABLE 5B

| Product Array | Verbal size design. (abbrev.) | Intended wearer hip meas. (mm) | Pant waist size (mm) | Waist size increase (mm) | Pant waist size increase % | Pant hip size to waist size difference (mm) | Pant Hip Size to Waist Size Ratio |
|---|---|---|---|---|---|---|---|
| Prototype | XS | 851 | 591 | | | 89 | 1.15 |
| Array 3 | S | 902 | 628 | 37 | 106.3% | 86 | 1.14 |
| Hipster | M | 953 | 666 | 38 | 106.0% | 83 | 1.13 |
| Decreasing | L | 1003 | 705 | 38 | 105.8% | 79 | 1.11 |
| Hip Size/ | XL | 1054 | 743 | 39 | 105.5% | 74 | 1.10 |
| Waist Size | 2XL | 1105 | 783 | 39 | 105.3% | 68 | 1.09 |
| Ratio with | 3XL | 1156 | 823 | 40 | 105.1% | 62 | 1.08 |
| Increasing | 4XL | 1207 | 863 | 40 | 104.9% | 54 | 1.06 |
| Size Desig. | 5XL | 1257 | 904 | 41 | 104.8% | 45 | 1.05 |

TABLE 6A

| Product Array | Verbal size design. (abbrev.) | Intended wearer hip meas. (mm) | Pant hip size (mm) | Hip size increase (mm) | Hip size increase % | Normal pressure at hip (psi) |
|---|---|---|---|---|---|---|
| Prototype | XS | 851 | 688 | | | 0.032 |
| Array 4 | S | 902 | 718 | 31 | 104.4% | 0.034 |
| Hipster | M | 953 | 748 | 29 | 104.0% | 0.036 |
| Increasing | L | 1003 | 775 | 28 | 103.7% | 0.038 |
| Pressure by | XL | 1054 | 801 | 26 | 103.4% | 0.040 |
| Size | 2XL | 1105 | 825 | 24 | 103.0% | 0.043 |
| | 3XL | 1156 | 848 | 23 | 102.8% | 0.045 |
| | 4XL | 1207 | 870 | 21 | 102.5% | 0.048 |
| | 5XL | 1257 | 889 | 20 | 102.3% | 0.051 |

TABLE 6B

| Product Array | Verbal size design. (abbrev.) | Intended wearer hip meas. (mm) | Pant waist size (mm) | Waist size increase (mm) | Pant waist size increase % | Pant hip size to waist size difference (mm) | Pant Hip Size to Waist Size Ratio |
|---|---|---|---|---|---|---|---|
| Prototype | XS | 851 | 598 | | | 90 | 1.15 |
| Array 4 | S | 902 | 632 | 33 | 105.6% | 87 | 1.14 |
| Hipster | M | 953 | 664 | 33 | 105.2% | 83 | 1.13 |
| Decreasing | L | 1003 | 697 | 32 | 104.9% | 78 | 1.11 |
| Hip Size/ | XL | 1054 | 728 | 32 | 104.5% | 73 | 1.10 |
| Waist Size | 2XL | 1105 | 759 | 31 | 104.2% | 66 | 1.09 |
| Ratio with | 3XL | 1156 | 789 | 30 | 104.0% | 59 | 1.08 |
| Increasing | 4XL | 1207 | 818 | 29 | 103.7% | 51 | 1.06 |
| Size Desig. | 5XL | 1257 | 847 | 28 | 103.5% | 42 | 1.05 |

It can be appreciated from the data in Tables 3A through 6B that pants in an array may be sized such that they exert consistent or increasing normal pressure, with each upward step in pant size designation. The data reflect that the prototypes follow the sizing schemes reflected in the mathematical expressions set forth above. It is believed that arrays of underwear pants following these sizing schemes will be more satisfactory to wearers purchasing underwear pants according to the size designations that are indicated for their body measurements.

As noted above, a second wearer preference identified by research is that, as wearers grow larger, they tend to prefer underwear pants in which the ratio between hip size and waist size of the underwear (measured as described below) decreases. Accordingly, a manufacturer may desire to size underwear pants of the same cut style designation in an array of pants of sequential, adjacent size designations, such that:

an article of a first size designation S1 has a first hip size HS1 and a first waist size WS1;

an article of a second size designation S2 has a second hip size HS2 and a second waist size WS2, wherein the hip sizes HS1 and HS2, and the waist sizes WS1 and WS2, have the following relationships:

$$HS2>HS1;$$

$$WS2>WS1; \text{ and}$$

$$(HS1-WS1)>(HS2-S2).$$

The manufacturer may include additional pants (of additional sequentially adjacent size designations) in the array, that follow the same pattern in continuing fashion.

Figure 6:
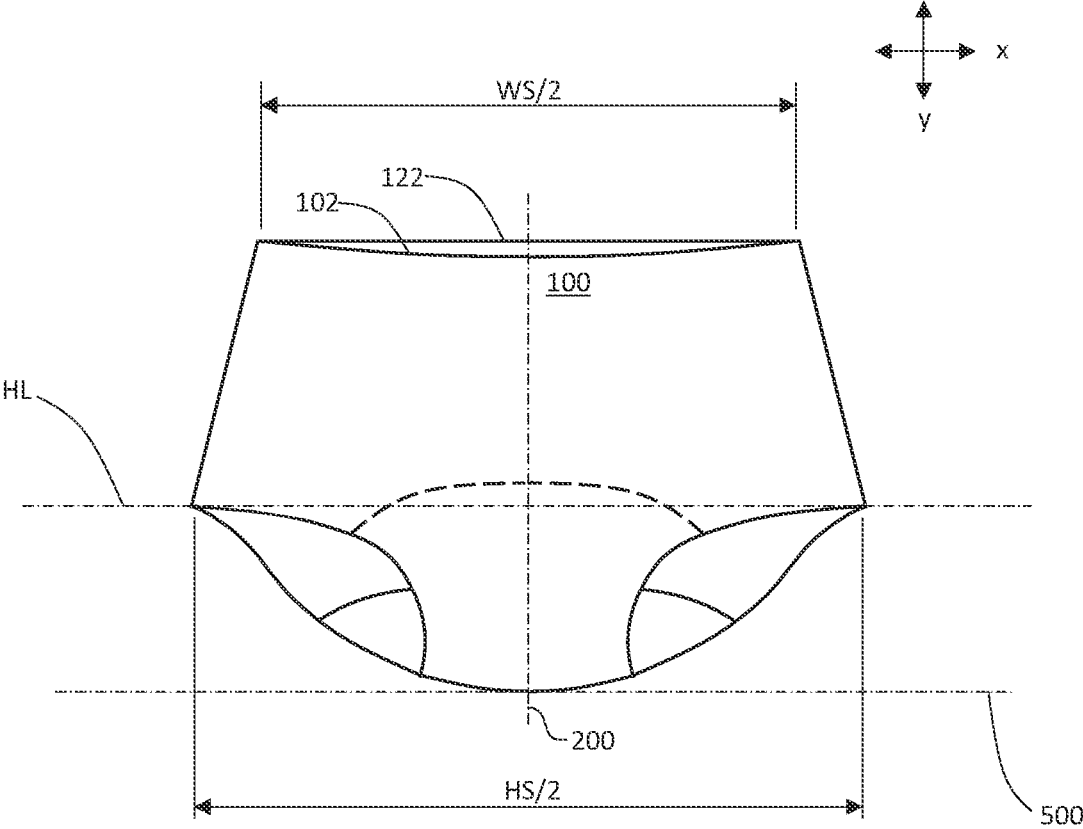
FIG. 6 is a simplified depiction of an example of a brief pant, as it would appear laid out flat on a horizontal planar surface, front waist portion facing up, with illustration relating to measurement of waist and hip sizes.
Figure 7:
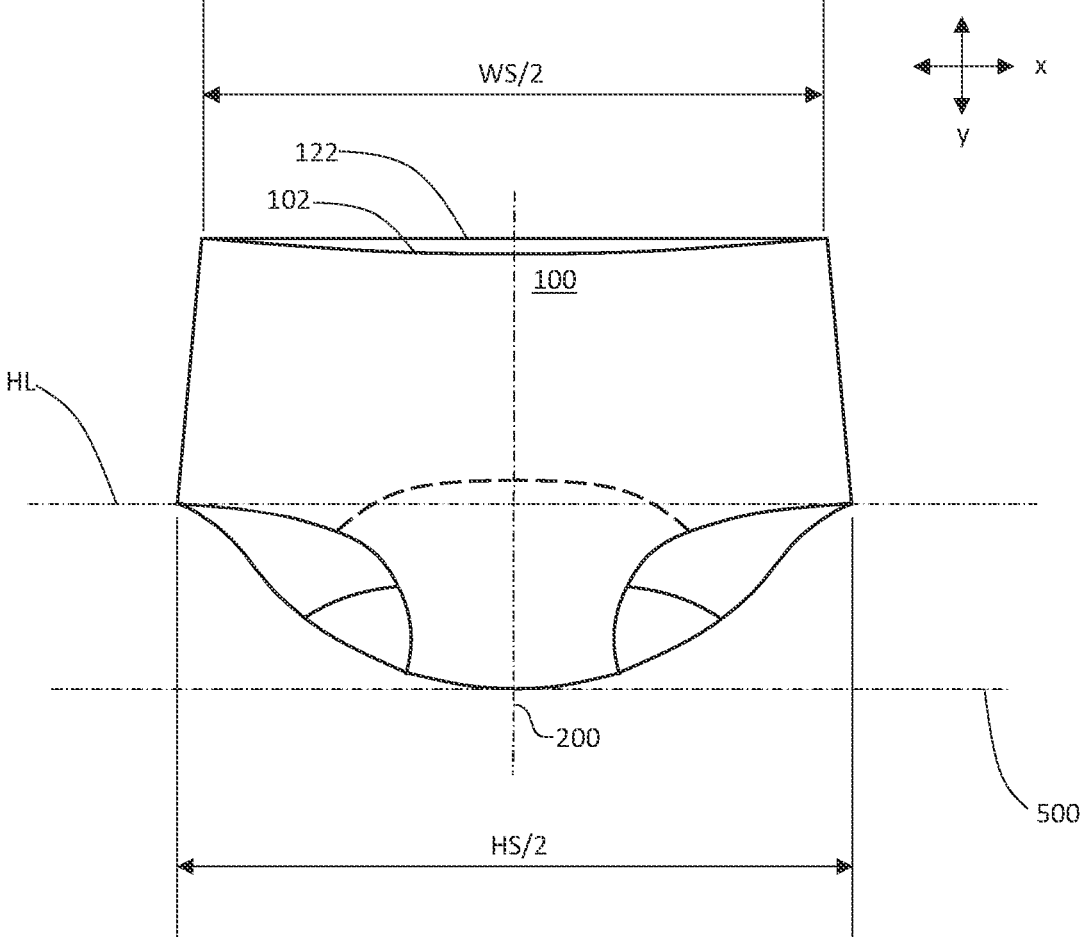
FIG. 7 is a simplified depiction of another example of a brief pant, as it would appear laid out flat on a horizontal planar surface, front waist portion facing up, with illustration relating to measurement of waist and hip sizes.

Expressed verbally, this means, generally, that with an increase of designated size of pants in the array, the difference between the hip size HS and the waist size WS decreases. Alternatively, or in addition, with an increase of designated size of pants in the array, the ratio of hip size HS to waist size WS approaches a value of 1.0, or a value even lower than 1.0. To illustrate, referring, for example, to the pants depicted in FIGS. 6 and 7, assume that the pant depicted in FIG. 6 is a smaller size designation pant and the pant depicted in FIG. 7 is a larger size designation pant within the same array. It can be seen that the ratio HS/2: WS/2 is a lesser value for the larger pant in FIG. 7, than the same ratio for the smaller pant in FIG. 6.

Figure 10:
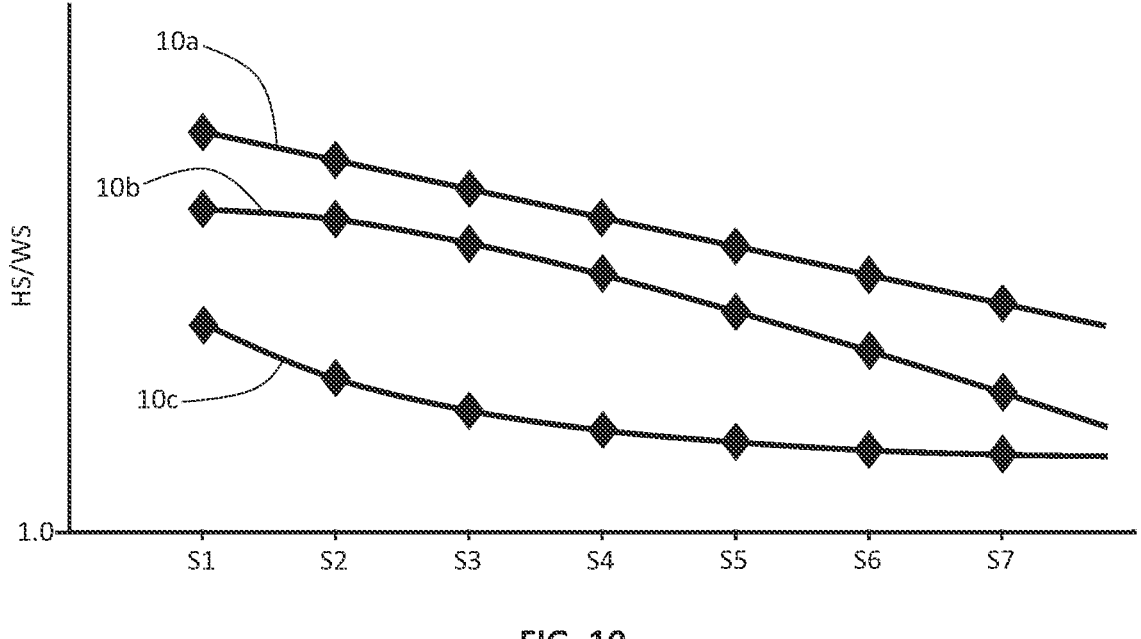
FIG. 10 is a schematic illustration of various possible plots of the ratio (hip size/waist size) (shown as HS/WS) versus pant size designations as contemplated herein.

Various possible conceptual examples of this relationship are illustrated in FIG. 10. Plot 10a represents a sizing scheme in which each size designation in the array (beginning with S2 and continuing to larger sizes) involves an equal step down in the ratio of hip size HS to waist size WS, from that of the preceding adjacent size designation in the array. Plots 10b and 10c represent sizing schemes in which each size designation in the array (beginning with S2 and continuing to larger sizes) involve changes in these ratios at changing rates. In Plot 10b, the ratio HS/WS decreases at an increasing rate with increases in adjacent sizes; in Plot 10c, the ratio HS/WS decreases at a decreasing rate with increases in adjacent sizes. In all three example plots, the ratio HS/WS trends toward 1.0, but it may be appreciated that the ratio may also decrease to values below 1.0 as designated sizes become larger.

Sizing underwear pants in an array of pants of designated sizes according to this scheme not only provides for better comfort of fit, generally, as wearer body measurements grow larger, but also helps prevent flipping over of the waistband of the underwear pants for the relatively larger-measurement wearer when, for example, the wearer bends at the waist or sits. This feature avoids concentration of pressure that can otherwise occur when a waist band flips over, and thereby further enhances comfort for wearers who have relatively larger body measurements.

Measurement Methods

For purposes herein, all measurements of hip size and waist size of a pant are made with the portion of the fabric subject to the measurement in a relaxed (i.e., unstretched) condition, with the pant laid out flat on a horizontal surface with all folds or wrinkles along the portion to be measured smoothed out.

If it is preferred to measure the pant in its fully assembled (i.e., not separated at the side portions or otherwise deconstructed) condition, the pant is laid on the horizontal surface with the front waist portion facing up.

Figure 8:
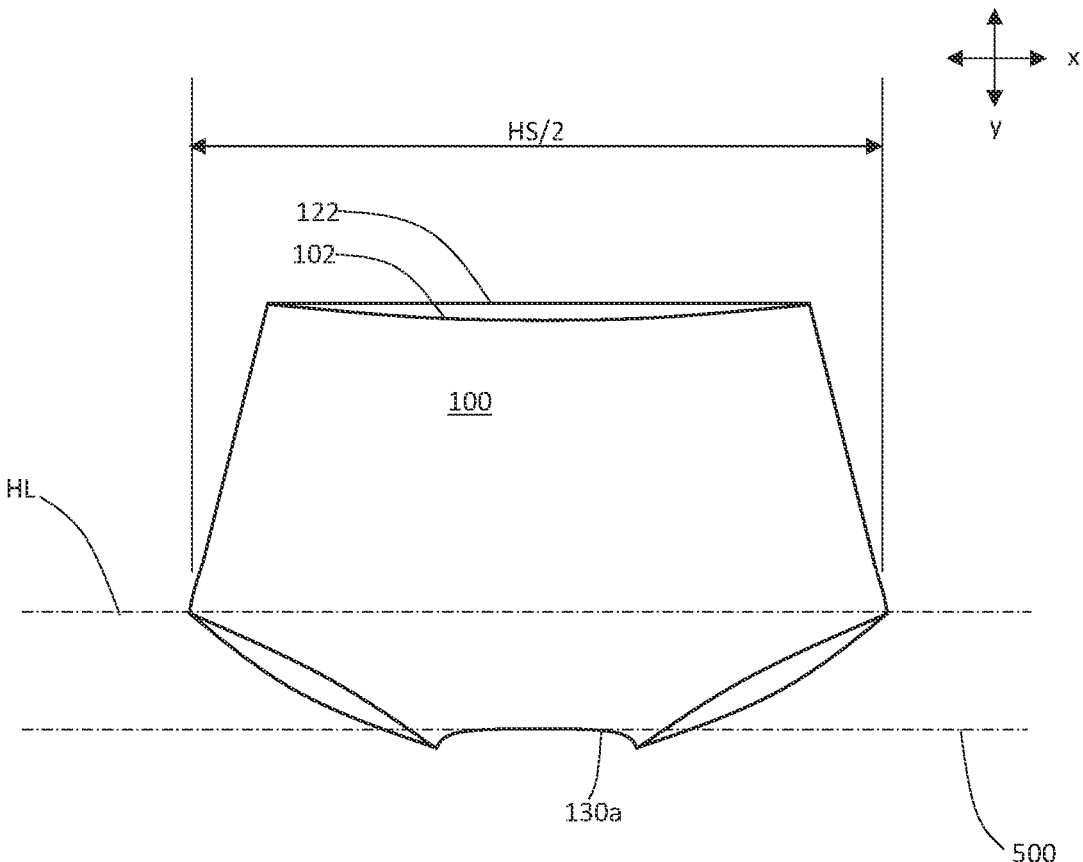
FIG. 8 is a simplified depiction of an example of a legged pant, as it would appear laid out flat on a horizontal planar surface, front waist portion facing up, with illustration relating to measurement of hip size.

The hip size HS of the pant is measured along a lateral line HL that is that is parallel with the crotch tangent line 500 as described and depicted herein, and drawn through the laterally widest portion of the pant, along the inside (wearer-facing) surfaces thereof. The hip size HS is the lateral dimension HS/2 of the pant along line HL, x 2. (See FIGS. 6-8.) If the pant is a legged pant with leg portions with laterally outermost portions present longitudinally below the crotch tangent line, then line HL is to be deemed to be the same as crotch tangent line 500.

The waist size WS of the pant is measured along a lateral line connecting the waist edges at the laterally widest extent thereof, but along the inside (wearer-facing) surfaces thereof. The waist size WS is the lateral dimension WS/2 of the pant, x 2. (See FIGS. 6-8.)

Alternatively, if it is preferred to measure the pant in its opened configuration (e.g., separated at the side seams 161 as suggested in, e.g., in FIG. 3), the opened pant is laid out flat on a horizontal surface with the wearer-facing surface facing up. The front and rear hip size components of the pant HSF and HSR are measured along lateral lines HL that are parallel with the lateral axis 300 as described and depicted herein, and drawn through the laterally widest portions of the pant in the front and rear waist portions, respectively, along the inside (wearer-facing) surfaces thereof, to the inside limits of the locations of the side seams. The hip size HS is the sum of front and rear hip size components, i.e., HS=HSF+HSR. (See FIG. 3.)

For waist size WS, the front and rear waist size components of the pant WSF and WSR are measured along lateral lines that are parallel with the lateral axis 300 as described and depicted herein, and drawn through the laterally widest portions of the waist edges, along the inside (wearer-facing) surfaces thereof, to the inside limits of the locations of the side seams. The waist size WS is the sum of front and rear waist size components, i.e., WS=WSF+WSR. (See FIG. 3.)

In view of the foregoing disclosure, the following non-limiting examples are contemplated herein. These and other examples may be claimed in the present application or additional applications claiming priority to the present application and based on the disclosure herein:

1. An array of durable absorbent pants including pants of at least six differing size designations having a common cut style designation, wherein:

a pant of a first size designation has a first hip size HS1, a pant of a second size designation adjacent the first size designation has a second hip size HS2, a pant of a third size designation adjacent the second size designation has a third hip size HS3, a pant of a fourth size designation adjacent the third size designation has a fourth hip size HS4, a pant of a fifth size designation adjacent the fourth size designation has a fifth hip size HSS, and a pant of a sixth size designation adjacent the fifth size designation has a sixth hip size HS6, wherein the hip sizes HS1 through HS6 have the following relationship:

$$[(HS2-HS1)/HS1] \geq [(HS3-HS2)/HS2] \geq [(HS4-HS3)/HS3] \geq [(HS5-HS4)]/HS4] \geq [(HS6-HS5)]/HS5].$$

2. The array of example 1 wherein the hip sizes HS1 through HS6 have one or more of the following relationships:

$$(HS2-HS1) \geq (HS3-HS2);$$

$$(HS3-HS2) \geq (HS4-HS3);$$

$$(HS4-HS3) \geq (HS5-HS4); \text{ and/or}$$

$$(HS5-HS4) \geq (HS6-HS5).$$

3. The array of either of examples 1 or 2, wherein:

the pant of the first size designation has a first waist size WS1, the pant of the second size designation has a second waist size WS2, the pant of the third size designation has a third waist size WS3, the pant of the fourth size designation has a fourth waist size WS4, and the pant of the fifth size designation has a fifth waist size WS5, wherein the waist sizes WS1 through WS5 have one or more of the following relationships:

$$[(WS2-S1)/WS1] \geq [(WS3-S2)/WS2];$$

$$[(WS3-S2)/WS2] \geq [(WS4-SS3)/WS3]; \text{ and/or}$$

$$(WS4-WS3)/WS3] \geq [(WS5-WS4)]/WS4].$$

4. The array of example 3 wherein the waist sizes WS1 through WS6 have one or more of the following relationships:

$$(WS2-WS1) \geq (WS3-WS2);$$

$$(WS3-WS2) \geq (WS4-WS3); \text{ and/or}$$

$$(WS4-WS3) \geq (WS5-WS4).$$

5. An array of durable absorbent underwear pants including pants of at least five differing size designations having a common cut style designation, wherein:

a pant of a first size designation has a first waist size WS1, a pant of a second size designation adjacent the first size designation has a second waist size WS2, a pant of a third size designation adjacent the second size designation has a third waist size WS3, a pant of a fourth size designation adjacent the third size designation has a fourth waist size WS4, and a pant of a fifth size designation adjacent the fourth size designation has a fifth waist size WS5, wherein the waist sizes WS1 through WS5 have the following relationship:

$$[(WS2-WS1)/WS1] \geq [(WS3-WS2)/WS2] \geq [(WS4-WS3)/WS3] \geq [(WS5-WS4)]/WS4].$$

6. The array of example 5 wherein the waist sizes WS1 through WS5 have one or more of the following relationships:

$$(WS2-WS1) \geq (WS3-WS2);$$

$$(WS3-WS2) \geq (WS4-WS3); \text{ and/or}$$

$$(WS4-WS3) \geq (WS5-WS4).$$

7 The array of either of examples 5 or 6 wherein:

the pant of the first size designation has a first hip size HS1, the pant of the second size designation has a second hip size HS2, the pant of the third size designation has a third hip size HS3, the pant of the fourth size designation has a fourth hip size HS4, and the pant of the fifth size designation has a fifth hip size HSS, wherein the hip sizes HS1 through HS5 have one or more of the following relationships:

$$[(HS2-HS1)/HS1] \geq [(HS3-HS2)/HS2];$$

$$[(HS3-HS2)/HS2] \geq [(HS4-HS3)/HS3]; \text{ and/or}$$

$$[(HS4-HS3)/HS3] \geq [(HS5-HS4)]/HS4].$$

8. The array of example 7 wherein the hip sizes HS1 through HS5 have one or more of the following relationships:

$$(HS2-HS1) \geq (HS3-HS2);$$

$$(HS3-HS2) \geq (HS4-HS3); \text{ and/or}$$

$$(HS4-HS3) \geq (HS5-HS4).$$

9. An array of durable absorbent underwear pants including pants of at least five differing size designations having a common cut style designation, wherein:

a pant of a first size designation has a first hip size HS1 and first waist size WS1, a pant of a second size designation adjacent the first size designation has a second hip size HS2 and second waist size WS2, a pant of a third size designation adjacent the second size designation has a third hip size HS3 and third waist size WS3, a pant of a fourth size designation adjacent the third size designation has a fourth hip size HS4 and fourth waist size WS4, and a pant of a fifth size designation adjacent the fourth size designation has a fifth hip size HS5 and fifth waist size WS5, wherein the hip sizes HS1 through HS5 have the following relationship:

$$[(HS2-HS1)/HS1] \geq [(HS3-HS2)/HS2] \geq [(HS4-HS3)/HS3] \geq [(HS5-HS4)]/HS4]; \text{ and}$$

wherein the waist sizes WS1 through WS5 have the following relationship:

$$[(WS2-WS1)/WS1] \geq [(WS3-WS2)/WS2] \geq [(WS4-WS3)/WS3] \geq [(WS5-WS4)]/WS4].$$

10. An array of durable absorbent underwear pants including pants of at least three differing size designations having a common cut style designation, wherein:

a pant of a first size designation has a first hip size HS1, a pant of a second size designation adjacent the first size designation has a second hip size HS2, and a pant of a third size designation adjacent the second size designation has a third hip size HS3, wherein each of the hip sizes HS1 through HS3 are equal to or larger than 760 mm; and wherein the hip sizes HS1 through HS3 have the following relationship:

$$[(HS2-HS1)/HS1] \geq [(HS3-HS2)/HS2].$$

11. The array of example 10 wherein the hip sizes HS1 through HS3 have the following relationship:

$$(HS2-HS1) \geq (HS3-HS2).$$

12. The array of either of examples 11 or 12 wherein the pant of the first size designation has a first waist size WS1, the pant of the second size designation has a second waist size WS2, and the pant of the third size designation has a third waist size WS3, wherein each of the waist sizes WS1 through WS3 are equal to or larger than 680 mm; and wherein the waist sizes WS1 through WS3 have the following relationship:

$$[(WS2-WS1)/WS1] \geq [(WS3-WS2)/WS2].$$

13. The array of example 12 wherein the waist sizes WS1 through WS3 have the following relationship:

$$(WS2-WS1) \geq (WS3-WS2).$$

14. An array of durable absorbent underwear pants including pants of at least three differing size designations having a common cut style designation, wherein:

a pant of a first size designation has a first waist size WS1, a pant of a second size designation adjacent the first size designation has a second waist size WS2, and a pant of a third size designation adjacent the second size designation has a third waist size WS3, wherein each of the waist sizes WS1 through WS3 are equal to or larger than 680 mm; and wherein the waist sizes WS1 through WS3 have the following relationship:

$$[(WS2-WS1)/WS1] \geq [(WS3-WS2)/WS2].$$

15. The array of example 12 wherein the waist sizes WS1 through WS3 have the following relationship:

$$(WS2-WS1) \geq (WS3-WS2).$$

16. An array of durable absorbent underwear pants including pants of at least four differing size designations having a common cut style designation, wherein:

a pant of a first size designation has a first hip size HS1 and a first waist size WS1;

a pant of a second size designation adjacent the first size designation has a second hip size HS2 and a second waist size WS2, a pant of a third size designation adjacent the second size designation has a third hip size HS3 and a third waist size WS3; and a pant of a fourth size designation adjacent the third size designation has a fourth hip size HS4 and a fourth waist size WS4, wherein the hip sizes HS1 through HS4 and waist sizes WS1 through WS4 have the following relationships:

$$HS4>HS3>HS2>HS1;$$

$$WS4>WS3>WS2>WS1; \text{ and}$$

$$(HS1-WS1)>(HS2-WS2)>(HS3-WS3)>(HS4-WS4).$$

17. The array of example 16 including at least five differing size designations having a common cut style designation, wherein:

a pant of a fifth size designation adjacent the fourth size designation has a fifth hip size HS5 and a fifth waist size WS5, wherein the hip sizes HS1 through HS5 and waist sizes WS1 through WS5 have the following relationships:

$$HS5>HS4>HS3>HS2>HS1;$$

$$WS5>WS4>WS3>WS2>WS1; \text{ and}$$

$$(HS1-WS1)>(HS2-WS2)>(HS3-WS3)>(HS4-WS4)>(HS5-WS5).$$

18. The array of either of examples 16 or 17 wherein the hip sizes HS1 through HS4 have one or more of the following relationships:

$$[(HS2-HS1)/HS1] \geq [(HS3-HS2)/HS2]; \text{ and/or}$$

$$[(HS3-HS2)/HS2] \geq [(HS4-HS3)/HS3].$$

19. The array of any of examples 16-18 wherein the waist sizes WS1 through WS4 have one or more of the following relationships:

$$[(WS2-WS1)/WS1] \geq [(WS3-WS2)/WS2]; \text{ and/or}$$

$$[(WS3-WS2)/WS2] \geq [(WS4-WS3)/WS3].$$

20. The array of any of the preceding examples wherein the outer structures of all of the pants in the array comprise a common fabric type.

21. The array of example 20 wherein the common fabric type is a knitted fabric.

22. The array of example 21 wherein the knitted fabric has a direction of greatest elongation capability oriented at least approximately parallel to a lateral direction of the pant in the array in which it is present.

23. The array of any of examples 20-22 wherein the common fabric type is elastically extensible.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the claims all such changes and modifications that are within the scope of this invention.

What is claimed is:

1. An array of durable absorbent underwear pants including pants of at least six differing size designations having a common cut style designation, wherein:

a pant of a first size designation has a first hip size HS1, a pant of a second size designation adjacent the first size designation has a second hip size HS2, a pant of a third size designation adjacent the second size designation has a third hip size HS3, a pant of a fourth size designation adjacent the third size designation has a fourth hip size HS4, a pant of a fifth size designation adjacent the fourth size designation has a fifth hip size HS5, and a pant of a sixth size designation adjacent the fifth size designation has a sixth hip size HS6, wherein the hip sizes HS1 through HS6 have the following relationship:

$$[(HS2-HS1)/HS1] \geq [(HS3-HS2)/HS2] \geq [(HS4-HS3)/HS3] \geq [(HS5-HS4)]/HS4] \geq [(HS6-HS5)]/HS5],$$
and wherein the hip sizes HS1 through HS6 have one or more of the following relationships:

$$(HS2-HS1) \geq (HS3-HS2);$$

$$(HS3-HS2) \geq (HS4-HS3);$$

$$(HS4-HS3) \geq (HS5-HS4); \text{ and/or}$$

$$(HS5-HS4) \geq (HS6-HS5).$$

2. The array of claim 1, wherein:

the pant of the first size designation has a first waist size WS1, the pant of the second size designation has a second waist size WS2, the pant of the third size designation has a third waist size WS3, the pant of the fourth size designation has a fourth waist size WS4, and the pant of the fifth size designation has a fifth waist size WS5, wherein the waist sizes WS1 through WS5 have one or more of the following relationships:

$$[(WS2-WS1)/WS1] \geq [(WS3-WS2)/WS2];$$

$$[(WS3-WS2)/WS2] \geq [(WS4-WS3)/WS3]; \text{ and/or}$$

$$[(WS4-WS3)/WS3] \geq [(WS5-WS4)]/WS4].$$

3. The array of claim 2 wherein the waist sizes WS1 through WS5 have one or more of the following relationships:

$$(WS2-WS1) \geq (WS3-WS2);$$

$$(WS3-WS2) \geq (WS4-WS3); \text{ and/or}$$

$$(WS4-WS3) \geq (WS5-WS4).$$

4. The array of claim 1 wherein the outer structures of all of the pants in the array comprise a common fabric type.

5. The array of claim 4 wherein the fabric has a direction of greatest elongation capability oriented at least approximately parallel to a lateral direction of the pant in the array in which it is present.

6. An array of durable absorbent underwear pants including pants of at least five differing size designations having a common cut style designation, wherein:

a pant of a first size designation has a first waist size WS1, a pant of a second size designation adjacent the first size designation has a second waist size WS2, a pant of a third size designation adjacent the second size designation has a third waist size WS3, a pant of a fourth size designation adjacent the third size designation has a fourth waist size WS4, and a pant of a fifth size designation adjacent the fourth size designation has a fifth waist size WS5, wherein WS5>WS4>WS3>WS2>WS1, and wherein the waist sizes WS1 through WS5 have the following relationship:

$$[(WS2-WS1)/WS1] \geq [(WS3-WS2)/WS2] \geq [(WS4-WS3)/WS3] \geq [(WS5-WS4)]/WS4], \text{ and}$$

wherein the waist sizes WS1 through WS5 have one or more of the following relationships:

$$(WS2-WS1) \geq (WS3-WS2);$$

$$(WS3-WS2) \geq (WS4-WS3); \text{ and/or}$$

$$(WS4-WS3) \geq (WS5-WS4).$$

7. The array of claim 6 wherein:

the pant of the first size designation has a first hip size HS1, the pant of the second size designation has a second hip size HS2, the pant of the third size designation has a third hip size HS3, the pant of the fourth size designation has a fourth hip size HS4, and the pant of the fifth size designation has a fifth hip size HS5, wherein the hip sizes HS1 through HS5 have one or more of the following relationships:

$$[(HS2-HS1)/HS1] \geq [(HS3-HS2)/HS2];$$

$$[(HS3-HS2)/HS2] \geq [(HS4-HS3)/HS3]; \text{ and/or}$$

$$[(HS4-HS3)/HS3] \geq [(HS5-HS4)]/HS4].$$

8. The array of claim 7 wherein the hip sizes HS1 through HS5 have one or more of the following relationships:

$$(HS2-HS1) \geq (HS3-HS2);$$

$$(HS3-HS2) \geq (HS4-HS3); \text{ and/or}$$

$$(HS4-HS3) \geq (HS5-HS4).$$

9. The array of claim 6 wherein the outer structures of all of the pants in the array comprise a common fabric type.

10. The array of claim 9 wherein the fabric has a direction of greatest elongation capability oriented at least approximately parallel to a lateral direction of the pant in the array in which it is present.

11. An array of durable absorbent underwear pants including pants of at least three differing size designations having a common cut style designation, wherein:

a pant of a first size designation has a first hip size HS1, a pant of a second size designation adjacent the first size designation has a second hip size HS2, and a pant of a third size designation adjacent the second size designation has a third hip size HS3, wherein each of the hip sizes HS1 through HS3 are equal to or larger than 760 mm;

wherein HS3>HS2>HS1, and wherein the hip sizes HS1 through HS3 have the following relationship:

$$[(HS2-HS1)/HS1] \geq [(HS3-HS2)/HS2], \text{ and}$$

27 wherein the pant of the first size designation has a first waist size WS1, the pant of the second size designation has a second waist size WS2, and the pant of the third size designation has a third waist size WS3, wherein each of the waist sizes WS1 through WS3 are equal to or larger than 680 mm; and wherein the waist sizes WS1 through WS3 have the following relationship:

$$[(WS2-WS1)/WS1] \geq [(WS3-WS2)/WS2].$$

12. The array of claim 11 wherein the hip sizes HS1 through HS3 have the following relationship:

$$(HS2-HS1) \geq (HS3-HS2).$$

13. The array of claim 11 wherein the waist sizes WS1 through WS3 have the following relationship:

$$(WS2-WS1) \geq (WS3-WS2).$$

14. An array of durable absorbent underwear pants including pants of at least four differing size designations having a common cut style designation, wherein:

a pant of a first size designation has a first hip size HS1 and a first waist size WS1;

a pant of a second size designation adjacent the first size designation has a second hip size HS2 and a second waist size WS2, a pant of a third size designation adjacent the second size designation has a third hip size HS3 and a third waist size WS3; and a pant of a fourth size designation adjacent the third size designation has a fourth hip size HS4 and a fourth waist size WS4,

28 wherein the hip sizes HS1 through HS4 and waist sizes WS1 through WS4 have the following relationships:

$$HS4>HS3>HS2>HS1;$$

$$WS4>WS3>WS2>WS1;\text{ and}$$

$$(HS1-WS1)>(HS2-WS2)>(HS3-WS3)>(HS4-WS4).$$

15. The array of claim 14 including at least five differing size designations having a common cut style designation, wherein:

a pant of a fifth size designation adjacent the fourth size designation has a fifth hip size HS5 and a fifth waist size WS5, wherein the hip sizes HS1 through HS5 and waist sizes WS1 through WS5 have the following relationships:

$$HS5>HS4>HS3>HS2>HS1;$$

$$WS5>WS4>WS3>WS2>WS1;\text{ and}$$

$$(HS1-WS1)>(HS2-WS2)>(HS3-WS3)>(HS4-WS4)>(HS5-WS5).$$

16. The array of claim 14 wherein the hip sizes HS1 through HS4 have one or more of the following relationships:

$$[(HS2-HS1)/HS1] \geq [(HS3-HS2)/HS2];\text{ and/or}$$

$$[(HS3-HS2)/HS2] \geq [(HS4-HS3)/HS3].$$

17. The array of claim 14 wherein the waist sizes WS1 through WS4 have one or more of the following relationships:

$$[(WS2-WS1)/WS1] \geq [(WS3-WS2)/WS2];\text{ and/or}$$

$$[(WS3-WS2)/WS2] \geq [(WS4-WS3)/WS3].$$

* * * * *